(12) United States Patent
Gollan

(10) Patent No.: US 12,194,289 B2
(45) Date of Patent: *Jan. 14, 2025

(54) TRANSCUTANEOUS ELECTRICAL MUSCLE STIMULATION DEVICE FOR THE TREATMENT OF PREMATURE EJACULATION OR ERECTILE DYSFUNCTION, AND METHODS OF USE THEREOF

(71) Applicant: Virility Medical Ltd., Nazareth (IL)

(72) Inventor: Tal Gollan, Ramat-Gan (IL)

(73) Assignee: VIRILITY MEDICAL LTD. (IL)

( * ) Notice: Subject to any disclaimer, the term of this patent is extended or adjusted under 35 U.S.C. 154(b) by 200 days.

This patent is subject to a terminal disclaimer.

(21) Appl. No.: 17/019,468

(22) Filed: Sep. 14, 2020

(65) Prior Publication Data

US 2021/0016078 A1    Jan. 21, 2021

Related U.S. Application Data

(63) Continuation of application No. 15/778,707, filed as application No. PCT/IB2016/001731 on Nov. 17, 2016, now Pat. No. 10,773,072.

(Continued)

(51) Int. Cl.
    *A61N 1/04*    (2006.01)
    *A61N 1/02*    (2006.01)
    *A61N 1/36*    (2006.01)

(52) U.S. Cl.
    CPC .............. *A61N 1/0452* (2013.01); *A61N 1/02* (2013.01); *A61N 1/0492* (2013.01);
    (Continued)

(58) Field of Classification Search
    CPC .............. A61N 1/0521; A61N 1/36007; A61N 1/3601; A61N 1/36014; A61N 1/3603;
    (Continued)

(56) References Cited

U.S. PATENT DOCUMENTS

| 5,562,717 A | 10/1996 | Tippey et al. |
| 8,876,696 B2 | 11/2014 | Mikhailenok et al. |

(Continued)

FOREIGN PATENT DOCUMENTS

| CA | 2913074 | 12/2014 |
| EP | 2237831 | 10/2010 |

(Continued)

OTHER PUBLICATIONS

Office Action Dated Apr. 12, 2021 From the Israel Patent Office Re. Application No. 259474 and Its Translation Into English. (6 Pages).

(Continued)

*Primary Examiner* — John R Downey
(74) *Attorney, Agent, or Firm* — ISUS INTELLECTUAL PROPERTY PLLC; Anthony Jason Mirabito

(57) ABSTRACT

In one embodiment, the present invention provides a device, wherein the device comprises a skin patch, configured to attach to the skin surface of the perineum of a subject suffering from premature ejaculation, wherein the skin patch contains electrodes configured to deliver electrical impulses transcutaneously to the bulbcavernosus muscle of the subject, wherein the transcutaneously delivered electrical impulses are configured to treat premature ejaculation.

23 Claims, 8 Drawing Sheets

Related U.S. Application Data

(60) Provisional application No. 62/377,010, filed on Aug. 19, 2016, provisional application No. 62/259,960, filed on Nov. 25, 2015.

(52) U.S. Cl.
CPC ..... *A61N 1/36007* (2013.01); *A61N 1/36014* (2013.01); *A61N 1/3603* (2017.08)

(58) Field of Classification Search
CPC .... A61N 1/36107; A61N 1/0452; A61N 1/02; A61N 1/0492
USPC .............................................. 607/39–41, 143
See application file for complete search history.

(56) References Cited

U.S. PATENT DOCUMENTS

| | | | |
|---|---|---|---|
| 9,149,634 | B2 | 10/2015 | Lee |
| 9,370,652 | B2 | 6/2016 | Lin et al. |
| 9,764,010 | B2 | 9/2017 | Nilsson Neijber |
| 10,773,072 | B2 | 9/2020 | Gollan |
| 2006/0020297 | A1 | 1/2006 | Gerber et al. |
| 2007/0055337 | A1 | 3/2007 | Tanrisever |
| 2008/0161874 | A1 | 7/2008 | Bennett et al. |
| 2009/0182393 | A1 | 7/2009 | Bachinski |
| 2010/0016759 | A1 | 1/2010 | Lavoisier |
| 2013/0006322 | A1 | 1/2013 | Tai |
| 2013/0116742 | A1 | 5/2013 | Lavoisier |
| 2014/0074179 | A1 | 3/2014 | Heldman et al. |
| 2014/0155954 | A1 | 6/2014 | Lee |
| 2014/0324120 | A1 | 10/2014 | Bogie et al. |
| 2015/0290450 | A1* | 10/2015 | Kolb ................. A61N 1/36007 607/148 |
| 2015/0335288 | A1 | 11/2015 | Toth et al. |
| 2016/0015553 | A1 | 1/2016 | Caldarone |
| 2016/0015962 | A1 | 1/2016 | Shokoueinejad Maragheh et al. |
| 2016/0263376 | A1 | 9/2016 | Yoo et al. |
| 2016/0303370 | A1 | 10/2016 | Sharma |
| 2017/0014632 | A1 | 1/2017 | Kimura |
| 2018/0043157 | A1 | 2/2018 | Sharma |
| 2018/0168919 | A1 | 6/2018 | Fung |
| 2018/0345003 | A1 | 12/2018 | Gollan |
| 2021/0236805 | A1 | 8/2021 | Gollan |
| 2021/0361941 | A1 | 11/2021 | Gollan et al. |

FOREIGN PATENT DOCUMENTS

| | | |
|---|---|---|
| EP | 3131622 | 2/2017 |
| JP | 08-501946 | 3/1996 |
| JP | 2000-167067 | 6/2000 |
| JP | 2011-519646 | 7/2011 |
| JP | 2011-213617 | 10/2011 |
| JP | 2016-523125 | 8/2016 |
| KR | 10-2011-030443 | 3/2011 |
| KR | 10-1416612 | 7/2014 |
| KR | 10-2016-0039575 | 4/2016 |
| RU | 2207162 | 6/2003 |
| RU | 2248228 | 3/2005 |
| RU | 2525619 | 8/2014 |
| WO | WO 2009/089014 A1 | 7/2009 |
| WO | WO 2011/155089 | 12/2011 |
| WO | WO 2012/116407 | 9/2012 |
| WO | WO 2016/069090 | 5/2016 |
| WO | WO 2017/075359 | 5/2017 |
| WO | WO 2017/089887 | 6/2017 |
| WO | WO 2019/130311 | 7/2019 |

OTHER PUBLICATIONS

Notification of Office Action and Search Report Dated Jan. 5, 2021 From the State Intellectual Property Office of the People's Republic of China Re. Application No. 201680068609.X and Its English Summary (18 Pages).
Notice of Allowance Dated Jul. 21, 2022 from US Patent and Trademark Office Re. U.S. Appl. No. 17/233,602. (9 pages).
Examination Report Dated Jun. 28, 2021 From the Australian Government, IP Australia Re. Application No. 2016359227. (2 Pages).
Communication Pursuant to Article 94(3) EPC Dated Oct. 7, 2021 From the European Patent Office Re. Application No. 16868090.8. (3 Pages).
Notice of Reasons for Rejection Dated Oct. 27, 2020 From the Japan Patent Office Re. Application No. 2018-525733 and Its Translation Into English. (5 Pages).
Interview Summary Dated Oct. 8, 2021 From the US Patent and Trademark Office Re. U.S. Appl. No. 17/233,602. (2 Pages).
Applicant-Initiated Interview Summary Dated Jan. 29, 2020 From the US Patent and Trademark Office Re. U.S. Appl. No. 15/778,707. (3 pages).
Final Official Action Dated Apr. 21, 2020 from the US Patent and Trademark Office Re. U.S. Appl. No. 15/778,707. (24 pages).
International Preliminary Report on Patentability Dated Jun. 7, 2018 From the International Bureau of WIPO Re. Application No. PCT/IB2016/001731. (11 Pages).
International Search Report and the Written Opinion Dated May 18, 2017 From the International Searching Authority Re. Application No. PCT/IB2016/001731. (15 Pages).
Official Action Dated Oct. 4, 2019 From the US Patent and Trademark Office Re. U.S. Appl. No. 15/778,707. (24 pages).
Search Report and Opinion Dated Jul. 13, 2020 From the Servico Publico Federal, Ministerio da Economia, Instituto Nacional da Propriedade Industrial do Brasil Re. Application No. BR112018010536-8. (7 Pages).
Supplementary European Search Report and the European Search Opinion Dated Jul. 2, 2019 From the European Patent Office Re. Application No. 16868090.8. (6 Pages).
Notification of Office Action Dated Jun. 18, 2021 From the State Intellectual Property Office of the People's Republic of China Re. Application No. 201680068609.X and Its Translation into English. (19 Pages).
Office Action Dated Feb. 3, 2022 From the Israel Patent Office Re. Application No. 259474 and Its Translation Into English. (7 Pages).
Official Action Dated Nov. 17, 2021 from US Patent and Trademark Office Re. U.S. Appl. No. 17/233,602. (32 pages).
Final Official Action Dated Mar. 4, 2022 from US Patent and Trademark Office Re. U.S. Appl. No. 17/233,602. (37 pages).
Official Action Dated Jul. 23, 2021 from the US Patent and Trademark Office Re. U.S. Appl. No. 17/233,602. (26 pages).
Examination Report Under Sections 12 & 13 of the Patents Act, 1970 and the Patents Rules, 2003 Dated May 17, 2021 From the Government of India, Intellectual Property India, Patents, Designs, Trade Marks, Geographical Indications, The Patent Office Re. Application No. 201837021589. 11 Pages).
Notice of Reason(s) for Rejection Dated May 11, 2021 From the Japan Patent Office Re. Application No. 2018-525733 and Its Translation Into English. (6 Pages).
Patent Examination Report Dated Nov. 21, 2020 From the Australian Government, IP Australia Re. Application No. 2016359227. (5 Pages).
Official Action Dated Mar. 29, 2023 from US Patent and Trademark Office Re. U.S. Appl. No. 16/957,752. (20 pages).
Examination Report Under Sections 12 & 13 of the Patents Act, 1970 and the Patents Rules, 2003 Dated Apr. 28, 2022 From the Government of India, Intellectual Property India, Patents, Designs, Trade Marks, Geographical Indications, The Patent Office Re. Application No. 202027032095 with Claims. (10 Pages).
Final Official Action Dated Nov. 15, 2022 from the US Patent and Trademark Office Re. U.S. Appl. No. 16/957,752. (16 pages).
International Preliminary Report on Patentability Dated Jul. 9, 2020 From the International Bureau of WIPO Re. Application No. PCT/IL2018/051402. (7 Pages).
International Search Report and the Written Opinion Dated Apr. 11, 2019 From the International Searching Authority Re. Application No. PCT/IL2018/051402. (10 Pages).

(56) References Cited

OTHER PUBLICATIONS

International Search Report and the Written Opinion Dated May 18, 2017 From the International Searching Authority Re. Application No. PCT/IB182016/001731. (17 Pages).
Notice of Reason(s) for Rejection Dated Jan. 4, 2023 From the Japan Patent Office Re. Application No. 2020-535215 and Its Translation Into English. (20 Pages).
Official Action Dated Apr. 27, 2022 from US Patent and Trademark Office Re. U.S. Appl. No. 16/957,752. (19 pages).
Request for Examination and Search Report Dated Mar. 1, 2022 From the Federal Government Institution, Federal Institute of Industrial Property of the Federal Service of Intellectual Property, Patents and Trademarks of the Russian Federation, FIPS Re. 2020124618 and Its Translation Into English. (16 Pages).
Supplementary European Search Report and the European Search Opinion Dated Aug. 4, 2021 From the European Patent Office Re. Application No. 18895004.2. (6 Pages).
American Psychiatric Association Diagnostic and Statistical Manual of Mental Disorders DSM-5™, Association Psychiatric Association, 5th Ed., III: 1-947, 2013. (Part 1).
American Psychiatric Association Diagnostic and Statistical Manual of Mental Disorders DSM-5™, Association Psychiatric Association, 5th Ed., III: 1-947, 2013. (Part 2).
American Psychiatric Association Diagnostic and Statistical Manual of Mental Disorders DSM-5™, Association Psychiatric Association, 5th Ed., III: 1-947, 2013. (Part 3).
American Psychiatric Association Diagnostic and Statistical Manual of Mental Disorders DSM-5™, Association Psychiatric Association, 5th Ed., III: 1-947, 2013. (Part 4).
American Psychiatric Association Diagnostic and Statistical Manual of Mental Disorders DSM-5™, Association Psychiatric Association, 5th Ed., III: 1-947, 2013. (Part 5).
American Psychiatric Association Diagnostic and Statistical Manual of Mental Disorders DSM-5™, Association Psychiatric Association, 5th Ed., III: 1-947, 2013. (Part 6).
American Psychiatric Association Diagnostic and Statistical Manual of Mental Disorders DSM-5™, Association Psychiatric Association, 5th Ed., III: 1-947, 2013. (Part 7).
American Psychiatric Association Diagnostic and Statistical Manual of Mental Disorders DSM-5™, Association Psychiatric Association, 5th Ed., III: 1-947, 2013. (Part 8).
American Psychiatric Association Diagnostic and Statistical Manual of Mental Disorders DSM-5™, Association Psychiatric Association, 5th Ed., III: 1-947, 2013. (Part 9).
American Psychiatric Association Diagnostic and Statistical Manual of Mental Disorders DSM-5™, Association Psychiatric Association, 5th Ed., III: 1-947, 2013. (Part 10).
American Psychiatric Association Diagnostic and Statistical Manual of Mental Disorders DSM-5™, Association Psychiatric Association, 5th Ed., III: 1-947, 2013. (Part 11).
American Psychiatric Association Diagnostic and Statistical Manual of Mental Disorders DSM-5™, Association Psychiatric Association, 5th Ed., III: 1-947, 2013. (Part 12).
American Psychiatric Association Diagnostic and Statistical Manual of Mental Disorders DSM-5™, Association Psychiatric Association, 5th Ed., III: 1-947, 2013. (Part 13).
American Psychiatric Association Diagnostic and Statistical Manual of Mental Disorders DSM-5™, Association Psychiatric Association, 5th Ed., III: 1-947, 2013. (Part 14).
American Psychiatric Association Diagnostic and Statistical Manual of Mental Disorders DSM-5™, Association Psychiatric Association, 5th Ed., III: 1-947, 2013. (Part 15).
American Psychiatric Association Diagnostic and Statistical Manual of Mental Disorders DSM-5™, Association Psychiatric Association, 5th Ed., III: 1-947, 2013. (Part 16).
American Psychiatric Association Diagnostic and Statistical Manual of Mental Disorders DSM-5™, Association Psychiatric Association, 5th Ed., III: 1-947, 2013. (Part 17).
American Psychiatric Association Diagnostic and Statistical Manual of Mental Disorders DSM-5™, Association Psychiatric Association, 5th Ed., III: 1-947, 2013. (Part 18).
American Psychiatric Association Diagnostic and Statistical Manual of Mental Disorders DSM-5™, Association Psychiatric Association, 5th Ed., III: 1-947, 2013. (Part 19).
American Psychiatric Association Diagnostic and Statistical Manual of Mental Disorders DSM-5™, Association Psychiatric Association, 5th Ed., III: 1-947, 2013. (Part 20).
American Psychiatric Association Diagnostic and Statistical Manual of Mental Disorders DSM-5™, Association Psychiatric Association, 5th Ed., III: 1-947, 2013. (Part 21).
American Psychiatric Association Diagnostic and Statistical Manual of Mental Disorders DSM-5™, Association Psychiatric Association, 5th Ed., III: 1-947, 2013. (Part 22).
American Psychiatric Association Diagnostic and Statistical Manual of Mental Disorders DSM-5™, Association Psychiatric Association, 5th Ed., III: 1-947, 2013. (Part 23).
Case-Lo et al. "Delayed Ejaculation: Symptoms, Causes, Diagnosis, Treatment, Complications, Outlook, Diet and DE", HealthLine, 11 P., Jul. 21, 2016.
Donatucci "Etiology of Ejaculation and Pathophysiology of Premature Ejaculation", The Journal of Sexual Medicine, 3(Suppl.4): 303-308, Sep. 2006.
Doucet et al. "Neuromuscular Electrical Stimulation for Skeletal Muscle Function", Yale Journal of Biology and Medicine 85(2): 201-215, Jun. 2012.
Eisenberg et al. "Anogenital Distance as a Measure of Human Male Fertility",Journal of Assisted Reproduction and Genetics 32(3):479-484, Mar. 2015.
Eisenberg et al. "The Relationship Between Anogenital Distance and Age", Andrology, 1(1): 90-93, Jan. 2013.
Porter "Delayed Ejaculation DSM-5 302.74 (N53.11)", Theravive, Therapedia, 3 P., 2019.
Zorba et al. "Autonomic Nervous System Dysfunction in Lifelong Premature Ejaculation: Analysis of Heart Rate Variability", Urology, 80(6):1283-1286, Dec. 2012.
Interview Summary Dated Feb. 7, 2023 from the US Patent and Trademark Office Re. U.S. Appl. No. 16/957,752. (2 pages).
Requisition by the Examiner Dated Jan. 9, 2023 From the Innovation, Science and Economic Development Canada, Canadian Intellectual Property Office Re. Application No. 3,004,513 and Claims. (14 pages).
Notice of Reason(s) for Rejection Dated Jun. 6, 2023 From the Japan Patent Office Re. Application No. 2020-535215 and Its Translation Into English. (5 Pages).
Relatório de Exame Tecnico [Technical Examination Report] Dated May 23, 2023 From the Serviço Público Federal, Ministério da Economia, Instituto Nacional da Propriedade Industrial do Brasil Re. Application No. BR 11 2018 010536 8 and Its Translation Into English. (6 Pages).
Grounds of Reason of Rejection Dated Nov. 16, 2023 From the Korean Intellectual Property Office Re. Application No. 10-2020-7021758 (8 Pages).
Machine Translation Dated Nov. 21, 2023 of Grounds of Reason of Rejection Dated Nov. 16, 2023 From the Korean Intellectual Property Office Re. Application No. 10-2020-7021758 (6 Pages).
English Summary Dated Sep. 28, 2023 of Notification of Office Action Dated Sep. 13, 2023 From the State Intellectual Property Office of the People's Republic of China Re. Application No. 201880090395.5. (5 pages).
Grounds of Reason of Rejection Dated Aug. 28, 2023 From the Korean Intellectual Property Office Re. Application No. 10-2018-7017550 and Its Summary Into English. (11 Pages).
Machine Translation Dated Sep. 13, 2023 of Grounds of Reason of Rejection Dated Aug. 28, 2023 From the Korean Intellectual Property Office Re. Application No. 10-2018-7017550. (6 Pages).
Notice of Allowance Dated Sep. 19, 2023 from the US Patent and Trademark Office Re. U.S. Appl. No. 16/957,752. (19 pages).
Notification of Office Action and Search Report Dated Sep. 13, 2023 From the National Intellectual Property Administration of the People's Republic of China Re. Application No. 201880090395.5. (10 Pages).

(56) References Cited

OTHER PUBLICATIONS

Relatório de Exame Tecnico Dated Oct. 10, 2023 From the Serviço Público Federal, Ministério da Economia, Instituto Nacional da Propriedade Industrial do Brasil Re. Application No. BR 11 2018 010536 8 and Its Translation Into English. (6 Pages).

Requisition by the Examiner Dated Oct. 18, 2023 From the Innovation, Science and Economic Development Canada, Canadian Intellectual Property Office Re. Application No. 3,004,513 and Claims. (18 pages).

* cited by examiner

TRANSCUTANEOUS ELECTRICAL MUSCLE STIMULATION DEVICE FOR THE TREATMENT OF PREMATURE EJACULATION OR ERECTILE DYSFUNCTION, AND METHODS OF USE THEREOF

RELATED APPLICATIONS

This application is a continuation of U.S. patent application Ser. No. 15/778,707 filed on May 24, 2018, which is a National Phase of PCT Patent Application No. PCT/IB2016/001731 having International Filing Date of Nov. 17, 2016, which claims the benefit of priority under 35 USC § 119(e) of U.S. Provisional Patent Application Ser. Nos. 62/259,960 filed on Nov. 25, 2015 and 62/377,010 filed on Aug. 19, 2016. The contents of the above applications are all incorporated by reference as if fully set forth herein in their entirety.

FIELD AND BACKGROUND OF THE INVENTION

Various embodiments of the present invention relate to devices and methods to treat sexual dysfunction. In particular, various embodiments of the present invention relate to devices and methods to treat premature ejaculation.

Treatments for premature ejaculation include, for example, selective serotonin reuptake inhibitors (SSRI's), botulinum neurotoxin, and desensitization of the penis.

SUMMARY OF THE INVENTION

In one embodiment, the present invention provides a device, wherein the device comprises a skin patch, configured to attach to the skin surface of the perineum of a subject suffering from premature ejaculation, wherein the skin patch contains electrodes configured to deliver electrical impulses transcutaneously to the bulbcavernosus muscle of the subject, wherein the transcutaneously delivered electrical impulses are configured to treat premature ejaculation.

In one embodiment, the electrical impulses are delivered transcutaneously to the neuromuscular junction of the nerve innervating the bulbcavernosus muscle. In one embodiment, the nerve innervating the bulbcavernosus muscle is the motor branch of the pudendal nerve.

In one embodiment, the present invention provides a device, wherein the device comprises a skin patch, configured to attach to the skin surface of the perineum of a subject suffering from erectile dysfunction, wherein the skin patch contains electrodes configured to deliver electrical impulses transcutaneously to the ischiocavernosus and bulbospongiosus muscles of the subject, wherein the transcutaneously delivered electrical impulses are configured to treat the erectile dysfunction.

In one embodiment, the electrical impulses are delivered transcutaneously to the neuromuscular junction of the nerves innervating the ischiocavernosus and bulbospongiosus muscles. In one embodiment, the nerve innervating the bulbcavernosus muscle is the motor branch of the pudendal nerve.

In one embodiment, the device comprises at least one electrode having a first surface configured to attach to the skin surface of the perineum of the subject, and a second surface, opposite to the first surface configured to attach to a pad, wherein the pad comprises electronic circuitry and a power supply configured to deliver electrical impulses transcutaneously to the bulbcavernosus muscle of the subject, wherein the surface area of the first surface of the at least one electrode is configured to deliver electrical impulses transcutaneously to the bulbcavernosus muscle of the subject at a level sufficient to treat premature ejaculation.

In one embodiment, the device comprises at least one electrode having a first surface configured to attach to the skin surface of the perineum of the subject, and a second surface, opposite the first surface configured to attach to a pad, wherein the pad comprises electronic circuitry and a power supply configured to deliver electrical impulses transcutaneously to the bulbcavernosus muscle of the subject, wherein the surface area of the first surface of the at least one electrode is configured to deliver electrical impulses transcutaneously to the ischiocavernosus and bulbospongiosus muscles of the subject at a level sufficient to treat the erectile dysfunction.

In one embodiment, the device has two electrodes.
In one embodiment, the device has four electrodes.
In one embodiment, the pad is configured to cover the entire perineum of the subject.
In one embodiment, the power supply is configured to last 60 minutes.
In one embodiment, the at least one electrode is configured to cover the entire perineum of the subject.
In one embodiment, the transcutaneously delivered electrical impulses are configured to treat premature ejaculation by delaying ejaculation.
In one embodiment, the transcutaneously delivered electrical impulses are configured to induce a continuous contraction of the bulbcavernosus muscle of the subject.
In one embodiment, the transcutaneously delivered electrical impulses are configured to treat erectile dysfunction by increasing penile rigidity, by increasing the contractility of the ischiocavernosus and bulbospongiosus muscles.
In one embodiment, the transcutaneously delivered electrical impulses are configured to treat erectile dysfunction by increasing penile rigidity by reducing penile venous leak.
In one embodiment, the increased contractility of the ischiocavernosus and bulbospongiosus muscles reduces penile venous leak by reducing the drainage of blood from the deep dorsal vein of the penis.
In one embodiment, the device is disposable.
In one embodiment, the present invention provides a method, wherein the method treats a subject suffering from premature ejaculation, comprising the steps of: (a) attaching the device according to some embodiments of the present invention to the skin surface of the perineum of the subject; and (b) delivering electrical impulses transcutaneously to the bulbcavernosus muscle of the subject, wherein the transcutaneously delivered electrical impulses are configured to treat premature ejaculation.
In one embodiment, the present invention provides a method, wherein the method treats a subject suffering from erectile dysfunction, comprising the steps of: (a) attaching the device according to some embodiments of the present invention to the skin surface of the perineum of the subject; and (b) delivering electrical impulses transcutaneously to the ischiocavernosus and bulbospongiosus muscles of the subject, wherein the transcutaneously delivered electrical impulses are configured to treat the erectile dysfunction.
In one embodiment, the device is attached to the skin surface of the perineum of the subject prior to sexual intercourse.
In one embodiment, the electrical impulses are delivered transcutaneously to the bulbcavernosus muscle of the subject until the subject ejaculates.

In one embodiment, the electrical impulses are delivered transcutaneously to the bulbcavernosus muscle of the subject until the subject wishes to ejaculate.

In one embodiment, the electrical impulses are a biphasic symmetrical wave.

In one embodiment, the frequency of the electrical impulses are from 1 to 100 Hz.

In one embodiment, the pulse width of an electrical impulse is from 10 to 500 μs.

In one embodiment, the interphase interval is from 1 to 150 μs.

In one embodiment, the current of the electrical impulses is from 1 to 60 mA.

In one embodiment, the electrical impulses inhibit rhythmic contractions of the bulbcavernosus muscle of the subject that are required for ejaculation.

In one embodiment, the electrical impulses induce a continuous contraction of the bulbcavernosus muscle of the subject.

In one embodiment, the continuous contraction of the bulbcavernosus muscle is a contraction selected from the group consisting of: tetanic, sub tetanic, sub tetanic contraction with smaller oscillations, continuous, and intermittent.

In one embodiment, the electrical impulses increase the contractility of the ischiocavernosus and bulbospongiosus muscles of the subject.

In one embodiment, the increased contractility of the ischiocavernosus and bulbospongiosus muscles is a contraction selected from the group consisting of: tetanic, sub tetanic, sub tetanic contraction with smaller oscillations, continuous, and intermittent.

BRIEF DESCRIPTION OF THE SEVERAL VIEWS OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

Figure 1:
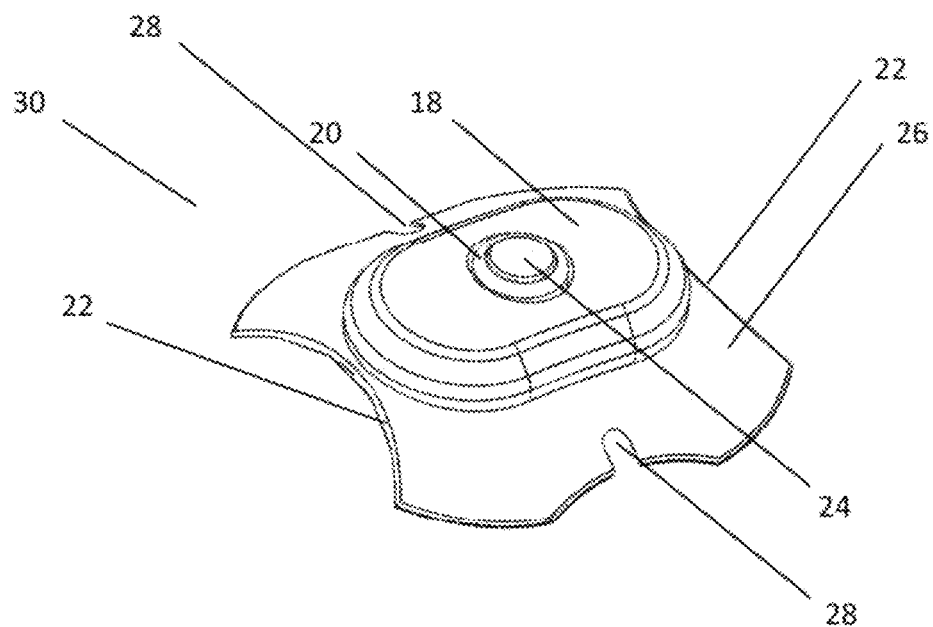
FIG. 1 shows a perspective view of a transcutaneous electrical muscle stimulation device according to some embodiments of the present invention.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

DESCRIPTION OF SPECIFIC EMBODIMENTS OF THE INVENTION

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, throughout the specification, the meaning of "a," "an," and "the" include plural references. The meaning of "in" includes "in" and "on."

The Bulbocavernousus muscle and the Bulbospongiosus muscle refer to the same muscle, and can be used interchangeably.

The Device

In some embodiments, the present invention provides a device, wherein the device comprises a skin patch, configured to attach to the skin surface of the perineum of a subject suffering from premature ejaculation, wherein the skin patch contains electrodes configured to deliver electrical impulses transcutaneously to the bulbcavernosus muscle of the subject, wherein the transcutaneously delivered electrical impulses are configured to treat premature ejaculation.

In some embodiments, the electrical impulses are delivered transcutaneously to the neuromuscular junction of the nerve innervating the bulbcavernosus muscle.

In some embodiments, the nerve innervating the bulbcavernosus muscle is the motor branch of the pudendal nerve.

In some embodiments, the present invention provides a device, wherein the device comprises a skin patch, configured to attach to the skin surface of the perineum of a subject suffering from erectile dysfunction, wherein the skin patch contains electrodes configured to deliver electrical impulses transcutaneously to the ischiocavernosus and bulbospongiosus muscles of the subject, wherein the transcutaneously delivered electrical impulses are configured to treat the erectile dysfunction.

In some embodiments, the electrical impulses are delivered transcutaneously to the neuromuscular junction of the nerves innervating the ischiocavernosus and bulbospongiosus muscles.

In some embodiments, the nerve innervating the bulbcavernosus muscle is the motor branch of the pudendal nerve.

In some embodiments, the device comprises at least one electrode having a first surface configured to attach to the skin surface of the perineum of the subject, and a second surface, opposite the first surface configured to attach to a pad, wherein the pad comprises electronic circuitry and a power supply configured to deliver electrical impulses transcutaneously to the bulbcavernosus muscle of the subject, wherein the surface area of the first surface of the at least one electrode is configured to deliver electrical impulses transcutaneously to the bulbcavernosus muscle of the subject at a level sufficient to treat the premature ejaculation.

In some embodiments, the device comprises at least one electrode having a first surface configured to attach to the skin surface of the perineum of the subject, and a second surface, opposite the first surface configured to attach to a pad, wherein the pad comprises electronic circuitry and a power supply configured to deliver electrical impulses transcutaneously to the bulbcavernosus muscle of the subject, wherein the surface area of the first surface of the at least one electrode is configured to deliver electrical impulses transcutaneously to the ischiocavernosus and bulbospongiosus muscles of the subject at a level sufficient to treat the erectile dysfunction.

In some embodiments, the device has two electrodes.

In some embodiments, the device has four electrodes.

Figure 2:
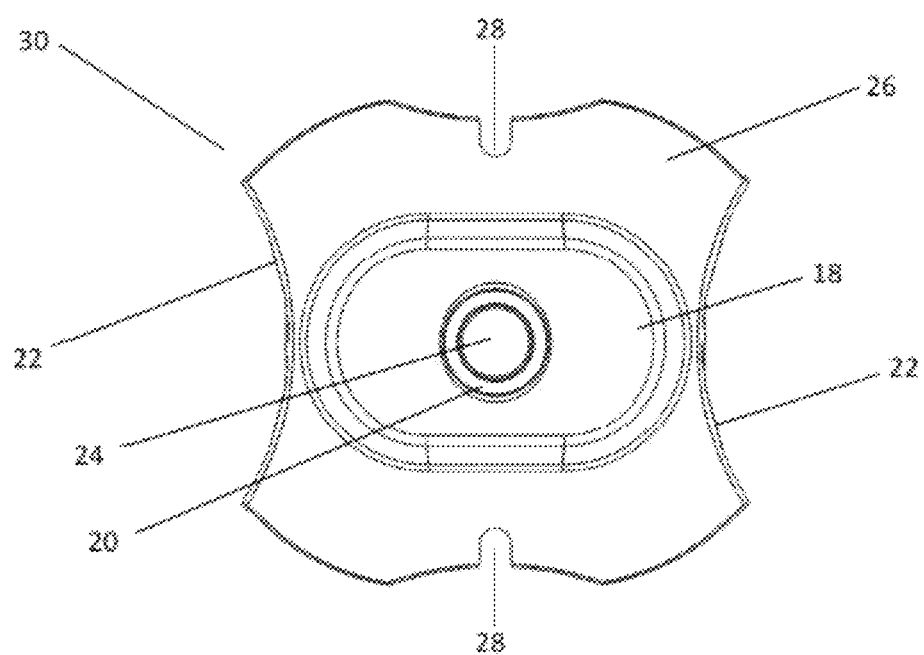
FIG. 2 shows a top view of a transcutaneous electrical muscle stimulation device according to some embodiments of the present invention.
Figure 3:
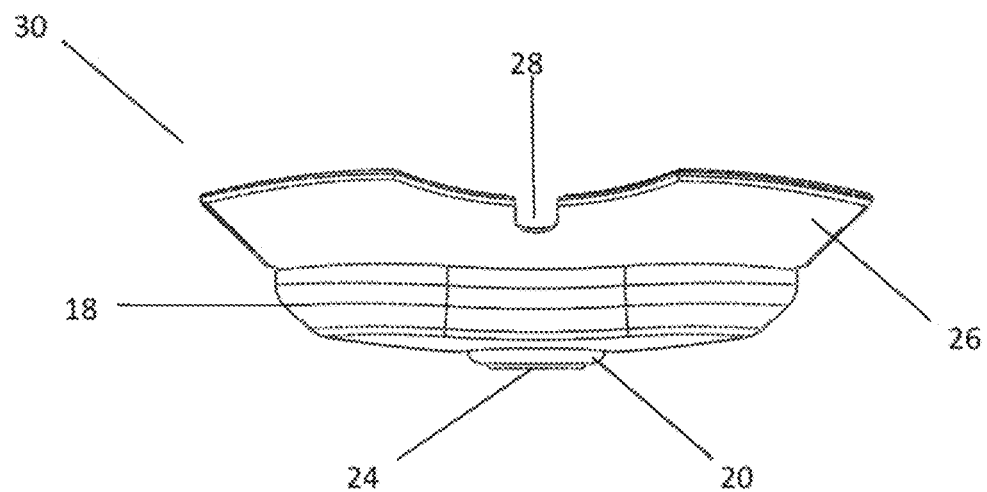
FIG. 3 shows a side view of a transcutaneous electrical muscle stimulation device according to some embodiments of the present invention.
Figure 4:
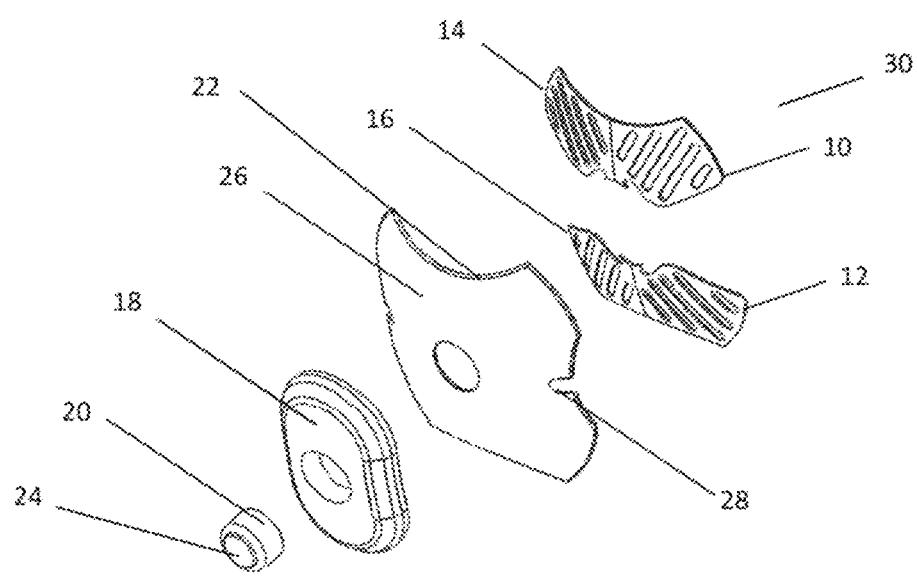
FIG. 4 shows a perspective exploded view of a transcutaneous electrical muscle stimulation device according to some embodiments of the present invention.
Figure 5:
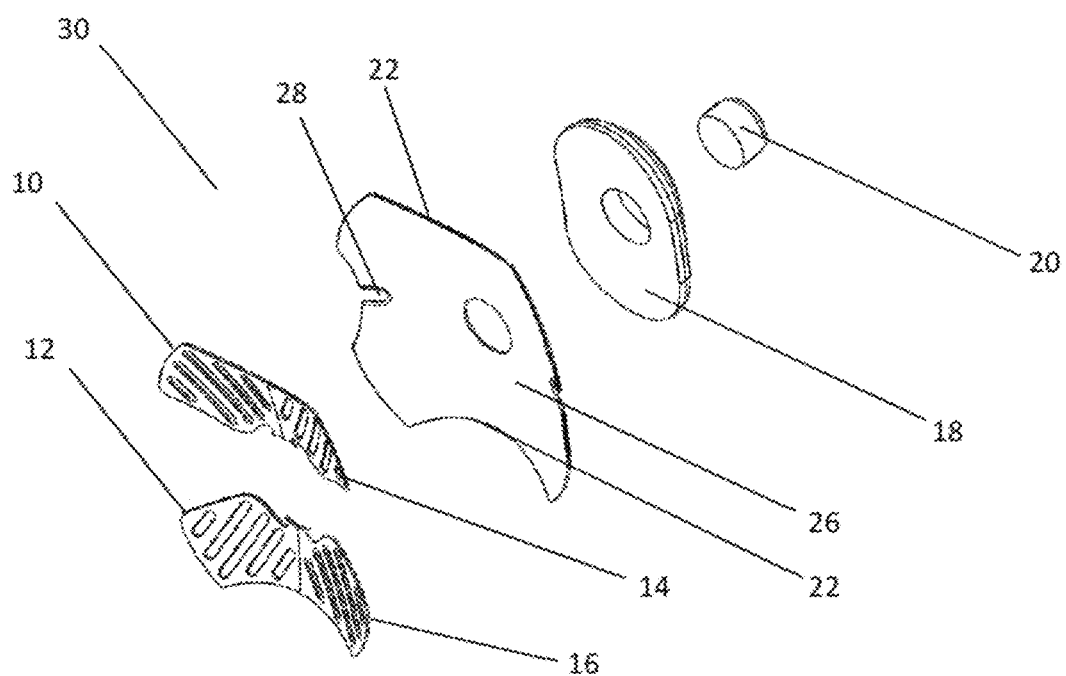
FIG. 5 shows a bottom perspective exploded view of a transcutaneous electrical muscle stimulation device according to some embodiments of the present invention.
Figure 6:
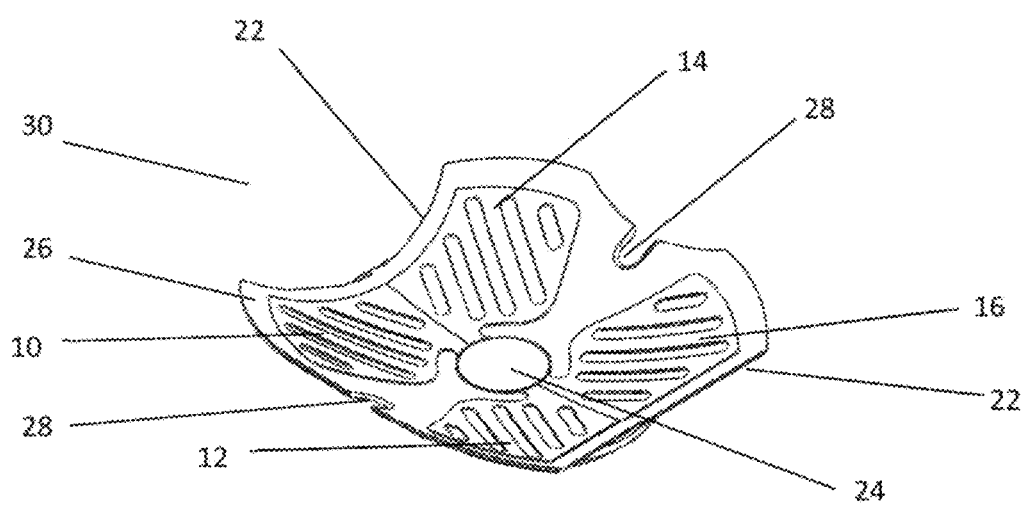
FIG. 6 shows a bottom perspective view of a transcutaneous electrical muscle stimulation device according to some embodiments of the present invention.
Figure 7:
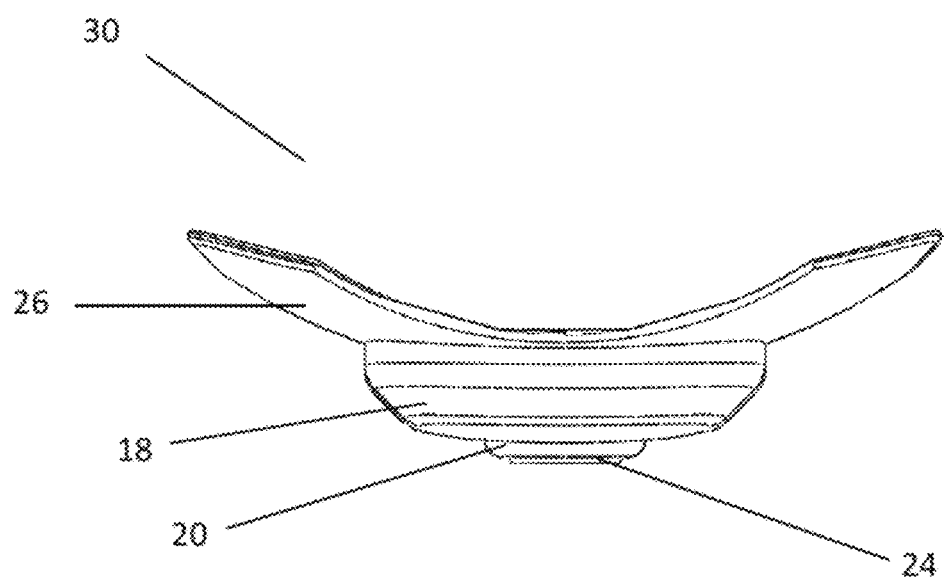
FIG. 7 a back view of a transcutaneous electrical muscle stimulation device according to some embodiments of the present Invention.
Figure 8:
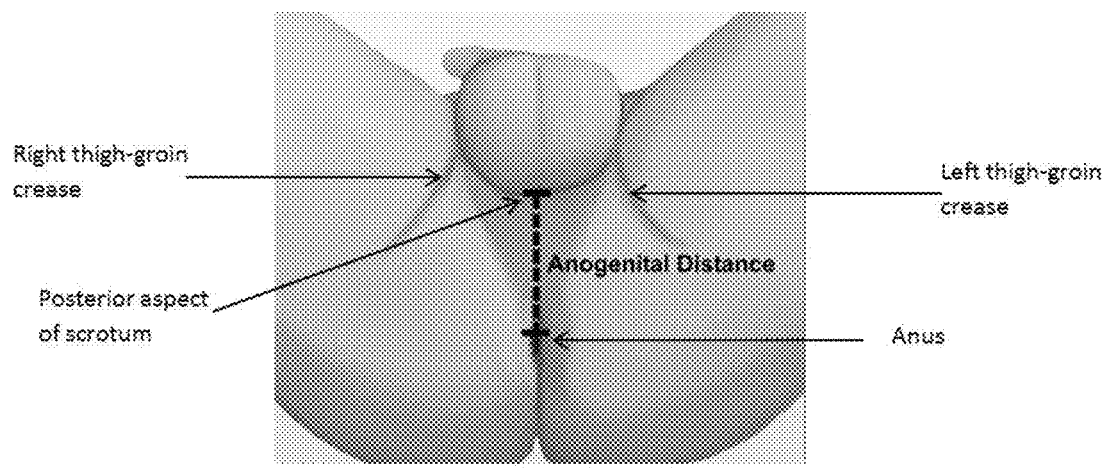
FIG. 8 shows a depiction of the perineum of the subject and the location where a device according to some embodiments of the present invention is attached.

Referring to FIGS. 1 through 7, in some embodiments, the device (30) comprises a first electrode (10), a second electrode (12), a third electrode (14), and a fourth electrode (16). In some embodiments, the first, second, third and fourth electrodes are attached to an electrode pad (26). In some embodiments, an electronic circuit housing (18) and a battery (20) is located on the side of the electrode pad (26) that is opposite to the side where the first, second, third and fourth electrodes are attached. In some embodiments, the side of the electrode pad (26) where the first, second, third and fourth electrodes are attached, is further configured to attach to the skin surface of the perineum of the subject.

In some embodiments, the side of the electrode pad (26) where the first, second, third and fourth electrodes are attached, is further configured to attach to the skin surface of the perineum of the subject via an adhesive.

In some embodiments, the pad is configured to cover the entire perineum of the subject.

In some embodiments, the at least one electrode is configured to cover the entire perineum of the subject.

In some embodiments, the electrode pad (26) is further configured with sections (22) that conform to the posterior aspect of the subject's scrotum. In some embodiments, the electrode pad (26) is further configured to not block the subject's anus. In some embodiments, the electrode pad (26) is further configured to conform with the subject's thigh-groin crease. In some embodiments, sections (28) enable the electrode pad (26) to flex with the subject's movements.

In some embodiments, the battery (20) is the power source of the desired electrical stimulation while the electronic circuitry, including a controller inside the electronic circuitry housing (18) generates the pattern of the electrical impulses, which can be direct or alternating current of various amplitudes and frequencies.

In some embodiments, the transcutaneously delivered electrical impulses are configured to treat premature ejaculation by delaying ejaculation of the subject.

In some embodiments, the transcutaneously delivered electrical impulses are configured to induce a continuous contraction of the bulbcavernosus muscle of the subject.

In some embodiments, the transcutaneously delivered electrical impulses are configured to treat erectile dysfunction by increasing penile rigidity, by increasing the contractility of the ischiocavernosus and bulbospongiosus muscles.

In some embodiments, the transcutaneously delivered electrical impulses are configured to treat erectile dysfunction by increasing penile rigidity by reducing penile venous leak.

In some embodiments, the increased contractility of the ischiocavernosus and bulbospongiosus muscles reduces penile venous leak by reducing the drainage of blood from the deep dorsal vein of the penis.

In some embodiments, the first electrode (10), second electrode (12), third electrode (14) and fourth electrode (16) transfer the electrical stimulation to the bulbospongiosus muscle via the skin of the patient.

In some embodiments, the first electrode (10), second electrode (12), third electrode (14) and fourth electrode (16) transfer the electrical stimulation to the ischiocavernosus and bulbospongiosus muscles via the skin of the patient.

The electrodes can be made from any suitable material, such as, for example, metal, carbon, a conductive gel, and the like.

In some embodiments, the maximal stimulation is less than the pain intensity threshold of the patient. In some embodiments, the purpose of the electrical stimulation is to induce a continuous contraction of the bulbospongiosus muscle. In some embodiments, the purpose of the electrical stimulation is to increase the contractility of the ischiocavernosus and bulbospongiosus muscles.

In some embodiments, the electronic circuitry housing (18) is used to isolate the electronic circuitry including a controller and battery (20) from the external environment. In some embodiments, the activation button (24) enables the subject to activate the device (30) during sexual intercourse.

In some embodiments, the electronic circuitry housing (18) is used to isolate the electronic circuitry including a controller and battery (20) from the external environment. In some embodiments, the activation button (24) enables the subject to activate the device (30) prior to penetration.

In some embodiments, the subject activates the device (3) by removing an insulator. In some embodiments, the subject activates the device (30) by (i) removing device (30) from a package, where in the removal of the device (30) from the package switches the patch from "off" to "standby"; and then (ii) activating the device (30) via a radio frequency signal.

In some embodiments, the device is disposable. In some embodiments, the power supply is configured to last 60 minutes. In some embodiments, the power supply is rechargeable. In some embodiments, the device is remotely activated. In some embodiments, the device is activated by placing the at least one electrode on the skin surface of the perineum of the subject.

In some the device (30) is disposed of when battery (20) is depleted. Optionally, the device may be configured to comprise both disposable and multiuse parts, for example the electronic circuitry including a controller may be a re-usable part.

In some embodiments, the electrode pad (26), the first electrode (10), the second electrode (12), the third electrode (14), and the fourth electrode (16) are affixed to the skin of the patient, between the anatomical landmarks of the posterior aspect of the scrotum and the anus, and between the left and right groin creases. In some embodiments, the scrotum fitting curved cuts (22) are designed to fit to the posterior aspect of the scrotum, thus enabling the patient to precisely position the device (30) and to stimulate specifically the bulbospongiosus muscle and the neuromuscular junction of the bulbospongiosus muscle and the muscular branch of the perineal nerve.

In some embodiments, device (30) is between 1 mm-10 mm in thickness, shorter in length than patient's anogenital distance, small enough to fit the anatomical size and proportions of the patient, and is flexible enough so it does not impose any discomfort to the patient. In some embodiments, slot cuts (28) are configured to allow the electrode pad (26) to easily bend, flex and conform to native perineum anatomy and movements.

In some embodiments, the device covers an area less than or equal to the perineum of the subject.

In some embodiments, the device width is from 5 to 50 mm smaller than the subject's anogential distance.

In some embodiments, the device length is from 5 to 50 mm smaller than the subject's groin crease distance.

Methods to Treat Premature Ejaculation or Erectile Dysfunction

In some embodiments, the present invention provides a method, wherein the method treats a subject suffering from premature ejaculation, comprising the steps of: (a) attaching the device according to some embodiments of the present invention to the skin surface of the perineum of the subject; and (b) delivering electrical impulses transcutaneously to the bulbcavernosus muscle of the subject, wherein the transcutaneously delivered electrical impulses are configured to treat the premature ejaculation.

In some embodiments, the present invention provides a method, wherein the method treats a subject suffering from erectile dysfunction, comprising the steps of: (a) attaching the device according to some embodiments of the present invention to the skin surface of the perineum of the subject; and (b) delivering electrical impulses transcutaneously to the ischiocavernosus and bulbospongiosus muscles of the subject, wherein the transcutaneously delivered electrical impulses are configured to treat the erectile dysfunction.

In some embodiments, the device is attached to the skin surface of the perineum of the subject prior to sexual intercourse. The device can be attached any time before intercourse, or, alternatively, during intercourse. The subject can manually activate the device after attachment. Or, alternatively, attachment of the device may activate the device.

Without intending to be limited to any particular theory, the ejaculatory process consists of two phases: (1) the emission phase, wherein sperm fluid is ejected into the posterior urethra by epithelial secretion and smooth muscle contractions; and (2) the expulsion phase, wherein sperm is ejected from the urethra due to the rhythmic contractions of the bulbocavernosus muscle.

Without intending to be limited to any particular theory, the transcutaneously delivered electrical impulses induce a continuous muscle contraction of the bulbocavernosus muscle during sexual intercourse. By inducing a continuous contraction of the bulbospongiosus muscle, its typical rhythmic contractions during ejaculation are diminished and/or subdued, thus postponing ejaculation. Electrical stimulation of other perineal muscles, such as the ischiocavernosus muscle, would have no positive effect on postponing premature ejaculation.

In some embodiments, the electrical impulses are delivered transcutaneously to the bulbcavernosus muscle of the subject until the subject ejaculates.

In some embodiments, the electrical impulses are delivered transcutaneously to the bulbcavernosus muscle of the subject until the subject wishes to ejaculate.

Without intending to be limited to any particular theory, the transcutaneously delivered electrical impulses are configured to treat erectile dysfunction by increasing penile rigidity, by increasing the contractility of the ischiocavernosus and bulbospongiosus muscles.

Without intending to be limited to any particular theory, the transcutaneously delivered electrical impulses are configured to treat erectile dysfunction by increasing penile rigidity by reducing penile venous leak. In some embodiments, the increased contractility of the ischiocavernosus and bulbospongiosus muscles reduces penile venous leak by reducing the drainage of blood from the deep dorsal vein of the penis.

In some embodiments, the properties of the electrical impulses are pre-programmed on the device, and the device transmits the pre-programmed electrical impulses. In some embodiments, the subject may select a particular pre-programmed electrical impulse to be transmitted. In some embodiments, the subject may program the device to transmit the desired electrical impulse.

In some embodiments, the electrical impulses are a biphasic symmetrical wave. In some embodiments, the electrical impulses are a square wave.

In some embodiments, the frequency of the electrical impulses are from 1 to 100 Hz. In some embodiments, the frequency is 90 Hz. In some embodiments, the frequency is 80 Hz. In some embodiments, the frequency is 70 Hz. In some embodiments, the frequency is 60 Hz. In some embodiments, the frequency is 50 Hz. In some embodiments, the frequency is 40 Hz. In some embodiments, the frequency is 30 Hz. In some embodiments, the frequency is 20 Hz. In some embodiments, the frequency is 10 Hz. In some embodiments, the frequency is 9 Hz. In some embodiments, the frequency is 8 Hz. In some embodiments, the frequency is 7 Hz. In some embodiments, the frequency is 6 Hz. In some embodiments, the frequency is 5 Hz. In some embodiments, the frequency is 4 Hz. In some embodiments, the frequency is 3 Hz. In some embodiments, the frequency is 100 Hz. In some embodiments, the frequency is 2 Hz. In some embodiments, the frequency is 1 Hz.

In some embodiments, the phase width of an electrical impulse is from 10 to 500 µs. In some embodiments, the phase width is 500 µs. In some embodiments, the phase width is 450. In some embodiments, the phase width is 400 µs. In some embodiments, the phase width is 350. In some embodiments, the phase width is 300 µs. In some embodiments, the phase width is 250 µs. In some embodiments, the phase width is 200 µs. In some embodiments, the phase width is 150 µs. In some embodiments, the phase width is 100 µs. In some embodiments, the phase width is 50 µs. In some embodiments, the phase width is 40 µs. In some embodiments, the phase width is 30 µs. In some embodiments, the phase width is 20 µs. In some embodiments, the phase width is 10 µs.

In some embodiments, the interphase interval is from 1 to 150 µs. In some embodiments, the interphase interval is 150 µs. In some embodiments, the interphase interval is 140 µs. In some embodiments, the interphase interval is 130 µs. In some embodiments, the interphase interval is 120 µs. In some embodiments, the interphase interval is 110 µs. In some embodiments, the interphase interval is 100 µs. In some embodiments, the interphase interval is 90 µs. In some embodiments, the interphase interval is 80 µs. In some embodiments, the interphase interval is 70 µs. In some embodiments, the interphase interval is 60 µs. In some embodiments, the interphase interval is 50 µs. In some embodiments, the interphase interval is 40 µs. In some embodiments, the interphase interval is 30 µs. In some embodiments, the interphase interval is 20 µs. In some embodiments, the interphase interval is 10 µs. In some embodiments, the interphase interval is 9 µs. In some embodiments, the interphase interval is 8 µs. In some embodiments, the interphase interval is 7 µs. In some embodiments, the interphase interval is 6 µs. In some embodiments, the interphase interval is 5 µs. In some embodiments, the interphase interval is 4 µs. In some embodiments, the interphase interval is 3 µs. In some embodiments, the interphase interval is 2 µs. In some embodiments, the interphase interval is 1 µs.

In some embodiments, the current of the electrical impulses is from 1 to 60 mA. In some embodiments, the current is 60 mA. In some embodiments, the current is 55 mA. In some embodiments, the current is 50 mA. In some embodiments, the current is 45 mA. In some embodiments, the current is 40 mA. In some embodiments, the current is 35 mA. In some embodiments, the current is 30 mA. In some embodiments, the current is 25 mA. In some embodiments, the current is 20 mA. In some embodiments, the current is 15 mA. In some embodiments, the current is 10 mA. In some embodiments, the current is 5 mA. In some embodiments, the current is 4 mA. In some embodiments, the current is 3 mA. In some embodiments, the current is 2 mA. In some embodiments, the current is 1 mA.

In some embodiments, the electrical impulses inhibit rhythmic concentrations of the bulbcavernosus muscle of the subject that are required for ejaculation.

In some embodiments, the electrical impulses induce a continuous contraction of the bulbcavernosus muscle of the subject.

In some embodiments, the continuous contraction of the bulbcavernosus muscle is a contraction selected from the group consisting of: tetanic, sub tetanic, continuous, and intermittent.

In some embodiments, the electrical impulses increase the contractility of the ischiocavernosus and bulbospongiosus muscles of the subject.

In some embodiments, the increased contractility of the ischiocavernosus and bulbospongiosus muscles is a contraction selected from the group consisting of: tetanic, sub tetanic, sub tetanic contraction with smaller oscillations, continuous, and intermittent.

Reference is now made to the following examples, which together with the above descriptions illustrate some embodiments of the invention in a non-limiting fashion.

EXAMPLES

Example 1: Methods of Treatment According to Some Embodiments of the Present Invention The patch provides a localized (as opposed to antidepressant systemic drugs), immediate/on-demand (as opposed to antidepressant drugs and desensitizing agents) and short term solution for premature ejaculation and/or erectile dysfunction. No long term therapeutic effect is expected.

Case 1: Prescription Product: The physician would prescribe the patient with a suitable patch, preconfigured and fitted for the patient's specific anatomy. Anatomical fitting means choosing patch size according to patient's own measurements and, measured by the physician: anogenital distance, groin crease distance, thickness of the fat layer between the skin and the muscle. Furthermore, thickness of the fat layer between the skin and the muscle can indicate the intensity of the electrical stimulation required for muscle contraction.

For example, in one embodiment, having fat layer thickness of 1 mm-5 mm may require stimulation intensity of 1 mA-20 mA, pulse width of 50 µs-200 µs, frequency of 1 Hz-100 Hz.

In other embodiment, having fat layer thickness of 4 mm-10 mm may require stimulation intensity of 15 mA-30 mA, pulse width of 150 µs-500 µs, frequency of 80 Hz-250 Hz.

In another embodiment, having fat layer thickness of 8 mm-20 mm may require stimulation intensity of 12 mA-50 mA, pulse width of 400 µs-1000 µs, frequency of 200 Hz-1 kHz.

The physician can deduce the required intensity by using surrogate markers, such as, for example Body Mass Index (BMI). The underlying rationale is that the higher the BMI, the thicker the fat layer between skin and muscle (which act as an insulator), thus requires higher stimulation intensity for effective muscle contraction. In one embodiment, having BMI of 15-20 would require stimulation intensity of 1 mA-20 mA, pulse width of 50 µs-200 µs, frequency of 1 Hz-100 Hz. In other embodiment, BMI of 18-25 would require stimulation intensity of 15 mA-30 mA, pulse width of 150 µs-500 µs, frequency of 80 Hz-250 Hz. Yet in another embodiment, BMI of 22-30 would require stimulation intensity of 12 mA-50 mA, pulse width of 400 µs-1000 µs, frequency of 200 Hz-1 kHz.

Case 2: Over-the-Counter Product: If the product is purchased over the counter (OTC), the user would have to be able to choose his own suitable stimulation intensity. Surrogate marker such as BMI is easily calculated or picked in a predefined table, and can indicate the required stimulation intensity.

In one embodiment, the patch can be adhered to the perineal skin immediately before sexual intercourse. In other embodiment, the patch can be adhered to the perineal skin between 1 and 60 minutes before sexual intercourse. Yet in another embodiment, the patch can be adhered to the perineal skin between 1 and 12 hours before sexual intercourse. Only before penetration (or after), the user can activate the electrical stimulation. This feature allows the preservation of spontaneity.

In one embodiment, the patch can generate electrical stimulation between 1 and 5 minutes. In other embodiment, the patch can generate electrical stimulation between 4 and 15 minutes. Yet in another embodiment, the patch can generate electrical stimulation between 10 and 60 minutes.

It is appreciated by persons skilled in the art that the present invention is not limited by what has been particularly shown and described hereinabove. Rather the scope of the present invention includes both combinations and sub combinations of various features described hereinabove as well as variations and modifications thereto which would occur to a person of skill in the art upon reading the above description and which are not in the prior art.

Publications cited throughout this document are hereby incorporated by reference in their entirety. Although the various aspects of the presently disclosed embodiments have been illustrated above by reference to examples and preferred embodiments, it will be appreciated that the scope of the presently disclosed embodiments are defined not by the foregoing description but by the following claims properly construed under principles of patent law.

In addition, citation or identification of any reference in this application shall not be construed as an admission that such reference is available as prior art to the presently disclosed embodiments. To the extent that section headings are used, they should not be construed as necessarily limiting.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A device, comprising:
   a skin patch comprising a body, wherein said skin patch has a surface configured to attach said skin patch to a skin surface of a perineum of a subject, wherein the skin patch body comprises:
   at least two electrodes in said body suitable to deliver electrical impulses transcutaneously; and
   an electronic circuitry including a controller electrically connected to said-at least two electrodes, wherein
      said at least two electrodes and said electronic circuitry are configured to deliver said electrical impulses between said at least two electrodes to a bulbospongiosus muscle of said subject, during sexual intercourse of said subject, with an intensity, frequency, current, and/or pulse width suitable to delay an ejaculation of said subject during said sexual intercourse; and
      said device is further configured to deliver said electrical impulses in response to receiving signals from a remote device.

2. The device of claim 1, wherein all of said device including said skin patch which includes said at least two electrodes and said electronic circuit housing, is shaped and sized to be attached to said skin surface of said subject.

3. The device of claim 2, wherein all of said device is shaped and sized to be attached to the skin surface of the subject.

4. The device of claim 1, wherein said device is configured to fit between and conform to each of the thigh-groin crease of a subject.

5. The device of claim 1, wherein said device does not include wires extending out from said skin patch.

6. The device of claim 1, wherein said device is configured to move between a standby state to an active state in response to said-remote device.

7. The device of claim 1, wherein the transcutaneously delivered electrical impulses are configured to induce a continuous contraction of the bulbospongiosus muscle of the subject.

8. The device of claim 1, further comprising bending sections comprising at least two curved cuts, each of said curved cuts is positioned at opposite sides of the skin patch to allow bending of said skin patch along an axis between said two curved cuts.

9. The device of claim 1, further comprising a battery with energy sufficient for generating said electrical impulses up to 30 minutes.

10. The device of claim 1, comprising bending sections that enable bending of said skin patch body which comprises said at least two electrodes, said a battery and said electronic circuitry, to conform said skin patch to anatomy of said perineum.

11. The device of claim 1, wherein said electronic circuitry is configured to receive radio frequency said signals from said remote device.

12. The device of claim 1, wherein when said subject wishes to ejaculate, the device is further configured to receive an input from said subject through said remote device to discontinue said electrical impulses in response to receiving said input.

13. A method, comprising:
   attaching a device, comprising a skin patch having at least two electrodes and an electronic circuitry in said skin patch, to a skin surface of a perineum of a subject, said at least two electrodes and electronic circuitry configured to deliver electrical impulses transcutaneously;
   receiving signals from a remote device; and
   delivering said electrical impulses between said at least two electrodes to a bulbospongiosus muscle of said subject during sexual intercourse, in response to said receiving of said signals;
   wherein said electrical impulses have have an intensity, frequency, current, and/or pulse width suitable to delay an ejaculation of said subject during said sexual intercourse.

14. The method of claim 13, wherein said attaching comprises attaching said device during said sexual intercourse.

15. The method of claim 13, wherein said delivering comprises delivering said electrical impulses for a time period of up to 30 minutes during said sexual intercourse.

16. The method of claim 13, wherein said electrical impulses are further configured to induce a continuous contraction of the bulbospongiosus muscle, said contraction selected from the group consisting of: tetanic, sub tetanic, sub tetanic contraction with smaller oscillations, continuous, and intermittent.

17. The method of claim 13, wherein the electrical impulses are a biphasic symmetrical wave.

18. The method of claim 13, wherein the frequency of the electrical impulses is from 1 to 100 Hz.

19. The method of claim 13, wherein the pulse width of said electrical impulses is from 10 to 500 μs.

20. The method of claim 13, wherein an interphase interval of said electrical impulses is from 1 to 500 μs.

21. The method of claim 13, wherein the current of the electrical impulses is from 1 to 60 mA.

22. The method of claim 13, wherein said attaching comprises attaching said device having bending sections that enable bending of the skin patch, to a skin surface of a perineum of the subject before or during sexual intercourse.

23. The method of claim 13, further comprising receiving an input from said subject through said remote device that said subject wishes to ejaculate; and discontinuing said electrical impulses in response to said receiving of said input.

\* \* \* \* \*